United States Patent
Horiuchi et al.

(10) Patent No.: US 10,973,476 B2
(45) Date of Patent: Apr. 13, 2021

(54) RADIATION DETECTION DEVICE

(71) Applicant: FUJIFILM Corporation, Tokyo (JP)

(72) Inventors: Hisatsugu Horiuchi, Kanagawa (JP); Shinsuke Noguchi, Kanagawa (JP); Masateru Tateishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 28 days.

(21) Appl. No.: 16/203,851

(22) Filed: Nov. 29, 2018

(65) Prior Publication Data
US 2019/0192093 A1 Jun. 27, 2019

(30) Foreign Application Priority Data
Dec. 22, 2017 (JP) .............................. JP2017-246650

(51) Int. Cl.
| | |
|---|---|
| *A61B 6/00* | (2006.01) |
| *G01T 1/20* | (2006.01) |
| *G01T 1/175* | (2006.01) |
| *G03B 42/00* | (2021.01) |

(52) U.S. Cl.
CPC ............ *A61B 6/4283* (2013.01); *G01T 1/175* (2013.01); *G01T 1/20* (2013.01); *G03B 42/00* (2013.01)

(58) Field of Classification Search
CPC ......... A61B 6/4283; A61B 6/44; G01T 1/175; G01T 1/20; G03B 42/00; G03B 42/04
See application file for complete search history.

(56) References Cited

U.S. PATENT DOCUMENTS

| | | | | |
|---|---|---|---|---|
| 6,700,126 | B2 * | 3/2004 | Watanabe | ............. G01T 1/2018 250/370.09 |
| 2004/0211909 | A1 | 10/2004 | Watanabe | |
| 2006/0157658 | A1 | 7/2006 | Watanabe | |
| 2007/0272873 | A1 * | 11/2007 | Jadrich | ...................... G01T 1/20 250/370.11 |
| 2009/0065703 | A1 * | 3/2009 | Jadrich | ................. G01T 1/2928 250/370.11 |

(Continued)

FOREIGN PATENT DOCUMENTS

| | | |
|---|---|---|
| JP | 2004-321568 A | 11/2004 |
| JP | 2005-195643 A | 7/2005 |

(Continued)

OTHER PUBLICATIONS

Office Action dated Feb. 16, 2021 in corresponding Japanese Patent Application No. 2017-246650, with English translation.

*Primary Examiner* — Marcus H Taningco
(74) *Attorney, Agent, or Firm* — Birch, Stewart, Kolasch & Birch, LLP

(57) ABSTRACT

A radiation detection device includes: a radiation detection panel; a housing in which the radiation detection panel is housed; a support member that is disposed between a surface of the radiation detection panel on a side opposite to a radiation incidence side and an inner surface of the housing; a plurality of columnar first protruding portions that are formed on a surface of the support member on an opposite side to a surface of the support member on a side of the radiation detection panel; and a second protruding portion that is formed at other region of the surface of the support member on the opposite side than regions of the surface of the support member on the opposite side at which the first protruding portions are formed as defined herein.

16 Claims, 12 Drawing Sheets

(56) References Cited

U.S. PATENT DOCUMENTS

| | | | |
|---|---|---|---|
| 2011/0272588 A1* | 11/2011 | Jadrich | G01T 1/20 |
| | | | 250/370.11 |
| 2012/0195409 A1 | 8/2012 | Suwa | |
| 2013/0153780 A1 | 6/2013 | Lee et al. | |
| 2014/0270092 A1* | 9/2014 | Ogura | G01T 1/2006 |
| | | | 378/189 |
| 2016/0081638 A1* | 3/2016 | Ogura | A61B 6/4283 |
| | | | 378/185 |
| 2016/0135764 A1* | 5/2016 | Wojcik | A61B 6/4233 |
| 2017/0258422 A1* | 9/2017 | Kim | A61B 6/4208 |

FOREIGN PATENT DOCUMENTS

| | | |
|---|---|---|
| JP | 2011-69740 A | 4/2011 |
| JP | 2014-171798 A | 9/2014 |
| JP | 2016-33516 A | 3/2016 |
| JP | 2016-182345 A | 10/2016 |

* cited by examiner

RADIATION DETECTION DEVICE

CROSS-REFERENCE TO RELATED APPLICATIONS

This application claims the benefit of Japanese Patent Application JP 2017-246650, filed Dec. 22, 2017, the entire content of which is hereby incorporated by reference, the same as if set forth at length.

BACKGROUND OF THE INVENTION

1. Field of the Invention

The present invention relates to a radiation detection device.

2. Description of the Related Art

An X-ray imaging apparatus that uses X-rays as radiation is known. The X-ray imaging apparatus has an X-ray detection device, which detects X-rays transmitted through a patient as a subject and generates an X-ray image signal based on the detected X-rays, and a console that communicates with the X-ray detection device.

As the X-ray detection device, there are a stationary type X-ray detection device fixed to an imaging table installed in a dedicated imaging room and a portable type X-ray detection device having a sensor panel housed in a portable housing.

The portable type X-ray detection device is called an electronic cassette and includes a radiation detection panel also called a flat panel detector (FPD), a memory for temporarily storing an X-ray image signal, and a communication unit for transmitting the X-ray image signal to the console.

Using the mobility of the electronic cassette, the electronic cassette is taken out of the imaging room and used. For example, the electronic cassette is used at the time of imaging at round visit for performing X-ray imaging while circulating a room where there is a patient who cannot move to the imaging room. The electronic cassette may be used outside the medical facility. The electronic cassette often receives a local load or impact due to its usage form.

JP2011-069740A and JP2016-033516A disclose X-ray detection devices each including a radiation detection panel, a support member for supporting the radiation detection panel from the rear surface side, and a housing in which the radiation detection panel and the support member are housed. In the X-ray detection device, a leg portion for receiving a load applied to the housing is provided between the support member and the housing.

As the configuration of the leg portion, JP2011-069740A discloses a configuration in which a plurality of columnar protruding portions are arranged so as to be spaced apart from each other, a configuration in which a protruding portion is formed in a frame shape, a configuration in which protruding portions are formed in a honeycomb or in a lattice pattern, and the like.

As the configuration of the leg portion, JP2016-033516A discloses a configuration in which a plurality of linear protruding portions are arranged in one direction and a configuration in which a plurality of columnar protruding portions are arranged in a two-dimensional manner.

SUMMARY OF THE INVENTION

A circuit board on which a circuit for driving the radiation detection panel, a circuit for storing the X-ray image signal, a circuit for communicating with a console, and the like are formed, a battery, and the like are built into the X-ray detection device.

As disclosed in JP2011-069740A and JP2016-033516A, in the configuration in which the protruding portion is provided between the support member and the housing, it is possible to increase the load bearing capacity by increasing the contact area between the protruding portion and the housing. However, as the contact area increases, the space between the support member and the housing formed by the protruding portion narrows. For this reason, the efficient arrangement of the circuit board, the battery, and the like using the space is difficult. On the other hand, in a case where priority is given to increasing the space, it is not possible to obtain a sufficient load bearing capacity.

In the configuration disclosed in JP2011-069740A, since the protruding portions are formed in a lattice pattern or the like, it is possible to secure the load bearing capacity, but it is not possible to secure a large space for arranging the circuit board or the battery.

In the configuration disclosed in JP2016-033516A, it is difficult to increase the number of protruding portions in order to secure a large space necessary for arranging the circuit board or the battery. Therefore, a further improvement in load bearing capacity becomes a problem.

The invention has been made in view of the above circumstances, and it is an object of the invention to provide a radiation detection device capable of improving both the load bearing capacity and the space use efficiency.

A radiation detection device of the invention comprises: a radiation detection panel; a housing in which the radiation detection panel is housed; a support member that is disposed between a surface of the radiation detection panel on a side opposite to a radiation incidence side and an inner surface of the housing; a plurality of columnar first protruding portions that are formed on a surface of the support member on an opposite side to a surface on the radiation detection panel side; and a second protruding portion that is formed at other region of the surface of the support member on the opposite side than regions of the surface of the support member on the opposite side at which the first protruding portions are formed so as to extend along the surface of the support member on the opposite side and that has a length in a direction, which is perpendicular to the surface of the support member on the radiation detection panel side, shorter than the first protruding portions.

According to the invention, it is possible to provide a radiation detection device capable of improving both the load bearing capacity and the space use efficiency.

DESCRIPTION OF THE PREFERRED EMBODIMENTS

Hereinafter, an embodiment of the invention will be described with reference to the diagrams.

Figure 1:
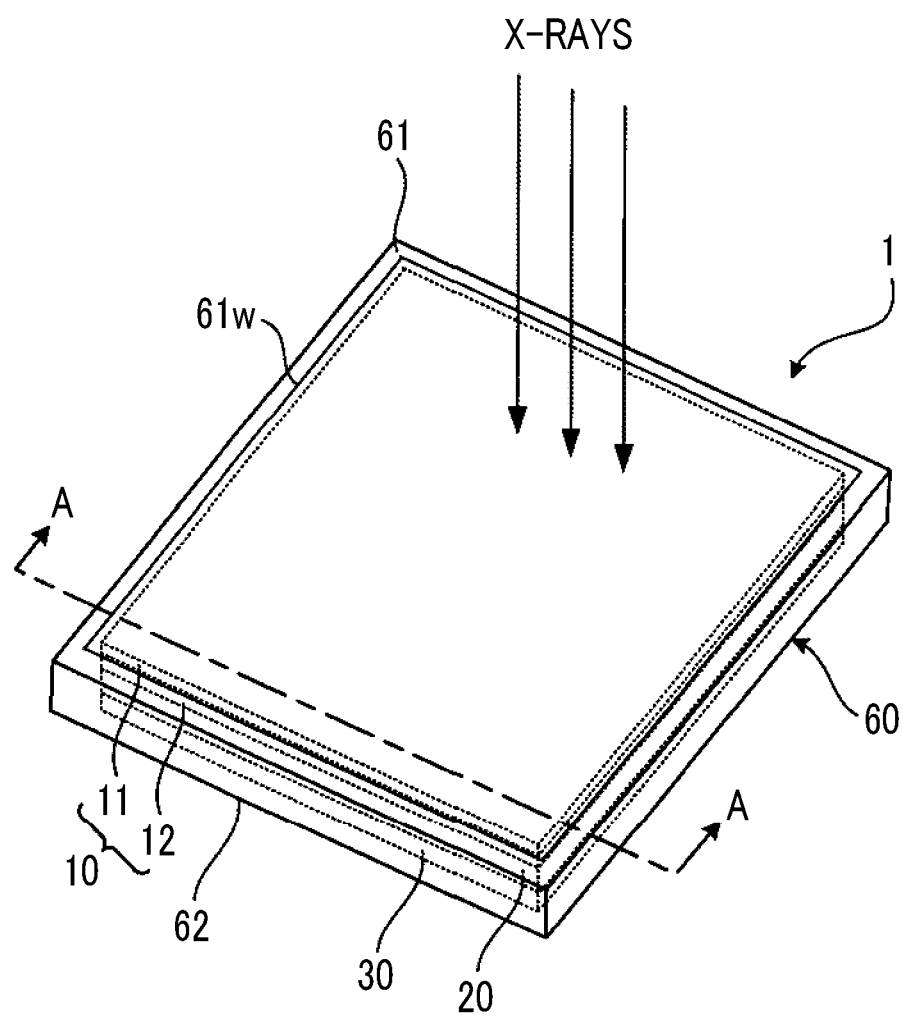
FIG. 1 is a diagram showing the schematic configuration of an electronic cassette 1 that is an embodiment of a radiation detection device of the invention.

FIG. 1 is a diagram showing the schematic configuration of an electronic cassette 1 that is an embodiment of a radiation detection device of the invention.

The electronic cassette 1 comprises a radiation detection panel 10, a support member 20 that supports the radiation detection panel 10 from the rear surface side (side opposite to the X-ray incidence side), a reinforcing member 30, and a portable housing 60 having a rectangular parallelepiped shape in which the radiation detection panel 10, the support member 20, and the reinforcing member 30 are housed.

The housing 60 is formed of a material having high rigidity, such as an aluminum alloy, a magnesium alloy, or a carbon fiber reinforced resin.

The housing 60 has, for example, a size complying with the international organization for standardization (ISO) 4090: 2001. A rectangular opening is formed on a front surface 61 of the housing 60, and a transmission plate 61w allowing X-rays as radiation to be transmitted therethrough is attached to the opening.

The electronic cassette 1 is positioned with the front surface 61 facing an X-ray source (not shown), and X-rays are emitted from above the front surface 61.

The radiation detection panel 10 is configured to include a scintillator 11 and a light detection substrate 12. The scintillator 11 and the light detection substrate 12 are laminated in order of the scintillator 11 and the light detection substrate 12 as viewed from the front surface 61 side on which X-rays are incident.

The scintillator 11 has a phosphor, such as CsI:Tl (thallium-activated cesium iodide) or GOS ($Gd_2O_2S$:Tb, terbium-activated gadolinium oxysulfide), and converts X-rays incident through the transmission plate 61w into visible light and emits the visible light.

A radiation detection panel may be used in which the light detection substrate 12 and the scintillator 11 are laminated in this order as viewed from the front surface 61 side on which X-rays are incident.

Alternatively, a direct conversion type radiation detection panel that directly converts X-rays into signal charges with a photoconductive film, such as amorphous selenium, may be used.

The light detection substrate 12 detects visible light emitted from the scintillator 11, and converts the visible light into an image signal.

Inside the housing 60 of the electronic cassette 1, in addition to the components described above, a circuit board 40 and a battery 50 as a power supply unit, which will be described later, are housed.

A circuit for controlling the driving of the light detection substrate 12, a circuit for processing the image signal output from the light detection substrate 12, a semiconductor memory, a communication interface for communicating with the outside, a power supply circuit, and the like are formed on the circuit board 40 housed in the housing 60.

The battery 50 housed in the housing 60 is configured to include one or more secondary rechargeable batteries, for example. The battery 50 supplies electric power to each unit of the electronic cassette 1. The secondary battery is, for example, a lithium ion secondary battery or a capacitor, such as an electric double layer capacitor or a lithium ion capacitor.

The support member 20 is a member that supports the radiation detection panel 10, and a material having high rigidity, such as an aluminum alloy, a magnesium alloy, or a carbon fiber reinforced resin, can be used.

The support member 20 is a member having a flat plate shape parallel to the imaging surface of the radiation detection panel 10, and is bonded to a surface of the radiation detection panel 10 opposite to the X-ray incidence side by an adhesive member, such as a double-sided tape. The support member 20 is supported by the housing 60.

The surface of the support member 20 bonded to the radiation detection panel 10 forms a surface (support surface 20a to be described later) of the support member 20 on the side of the radiation detection panel 10.

The reinforcing member 30 is disposed between the support member 20 and the inner surface (surface on the inner side with respect to the rear surface 62) of a housing 60, and functions to receive a load applied to the front surface 61 of the housing 60 and release the load to the rear surface 62 of the housing 60. The reinforcing member 30 functions to reinforce the rigidity of the support member 20. In addition, the reinforcing member 30 functions to form a space for arranging the components of the electronic cassette 1, such as a circuit board and a battery, between the support member 20 and the inner surface of the housing 60.

Figure 2:
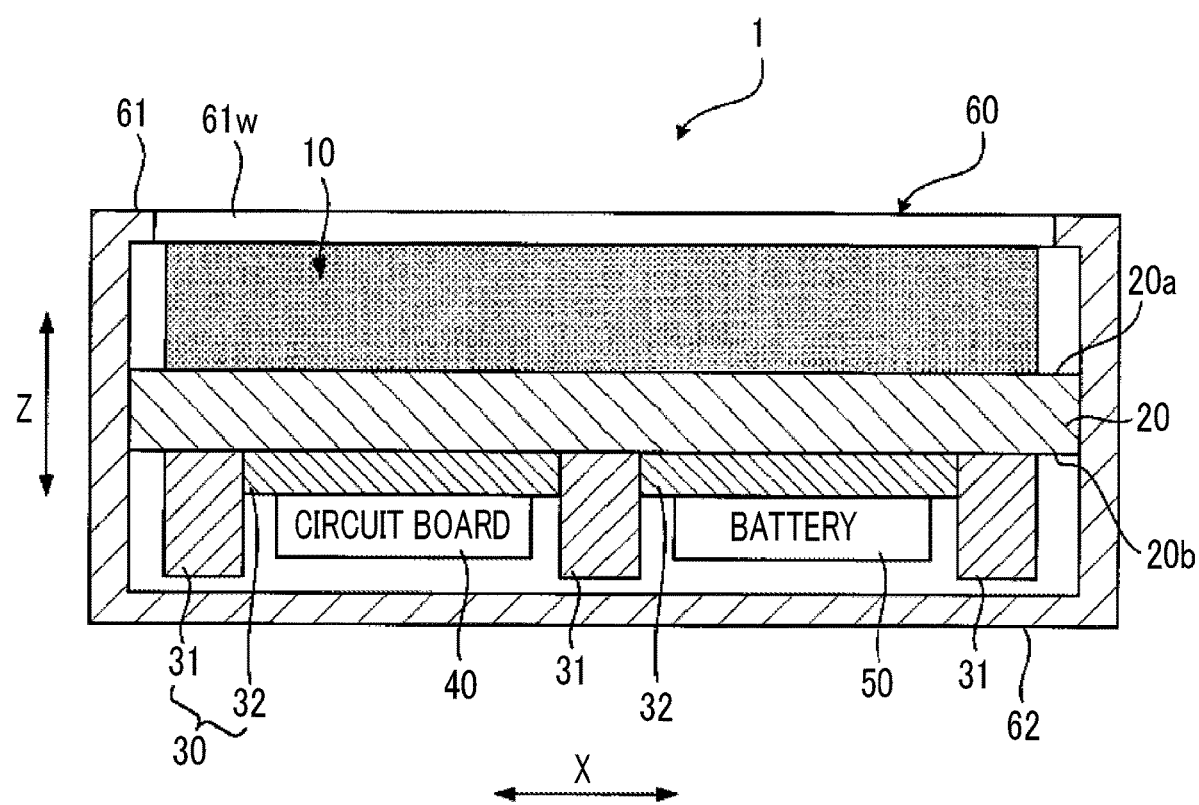
FIG. 2 is a schematic cross-sectional view of the electronic cassette 1 shown in FIG. 1 taken along the line A-A.
Figure 3:
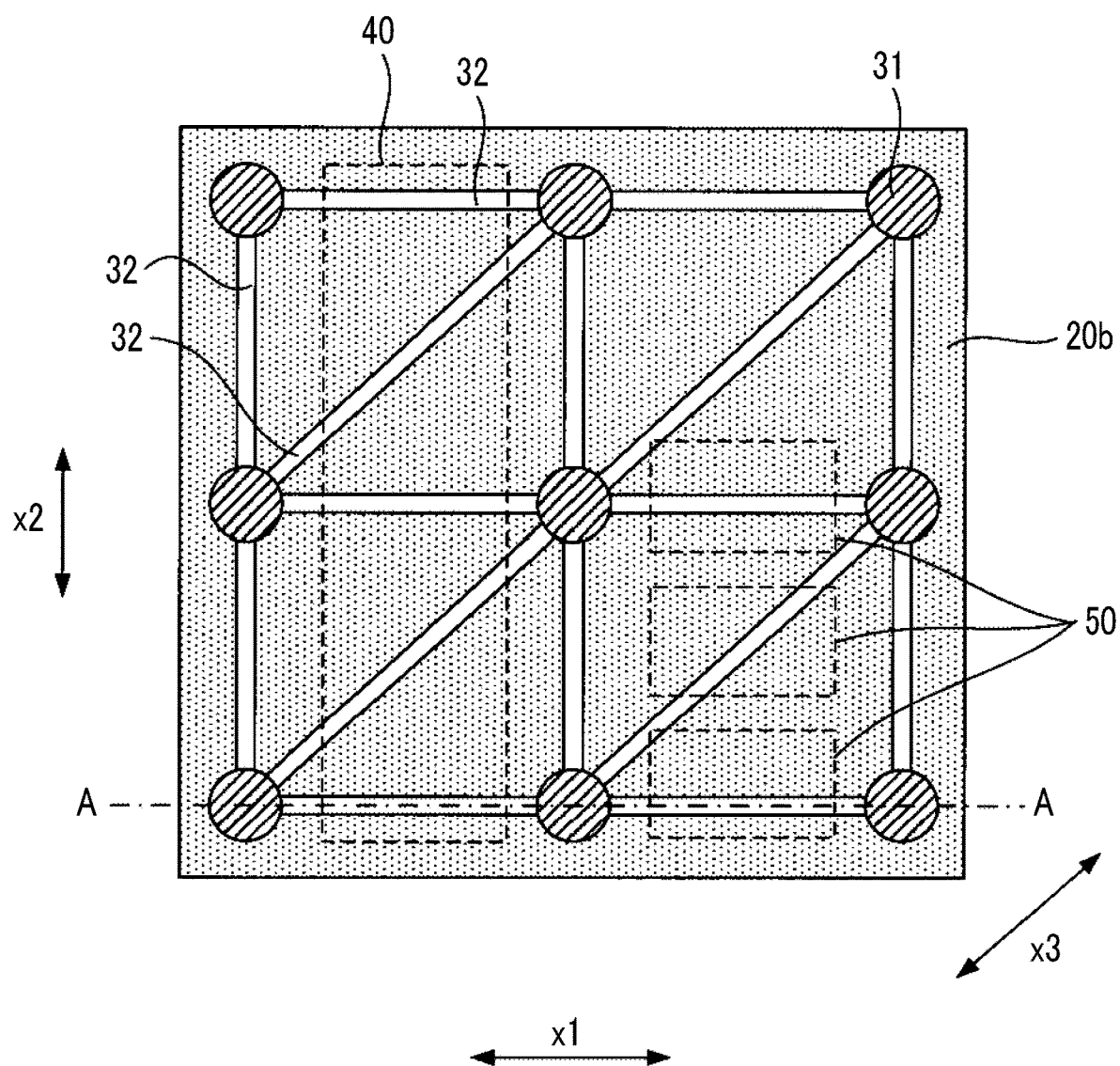
FIG. 3 is a plan view of a support member 20 and a reinforcing member 30 of the electronic cassette 1 shown in FIG. 1 as viewed from a side opposite to an X-ray incidence side.

FIG. 2 is a schematic cross-sectional view of the electronic cassette 1 shown in FIG. 1 taken along the line A-A. FIG. 3 is a plan view of the support member 20 and the reinforcing member 30 of the electronic cassette 1 shown in FIG. 1 as viewed from the side opposite to the X-ray incidence side.

FIG. 2 corresponds to a cross section taken along the line A-A shown in FIG. 3. In FIG. 2, a direction Z perpendicular to the support surface 20a of the support member 20 that supports the radiation detection panel 10 and a direction X parallel to the support surface 20a are shown.

As shown in FIGS. 2 and 3, the reinforcing member 30 is formed by a plurality of columnar first protruding portions 31 (in the example shown in FIG. 3, nine first protruding portions 31), which is formed on a surface 20b of the support member 20 opposite to the support surface 20a that supports the radiation detection panel 10, and a second protruding portion 32 that is formed in a region of the surface 20b of the support member 20 excluding a region, in which the first protruding portion 31 is formed, so as to extend along the surface 20b and that has a length in the direction Z shorter than the first protruding portion 31.

The first protruding portion 31 is a columnar member having a length in the direction Z of, for example, about 5 mm to 10 mm in order to secure a space between the support member 20 and the rear surface 62 of the housing 60. The first protruding portion 31 may have a columnar shape. For example, the first protruding portion 31 may have a prism shape.

In the example shown in FIG. 2, a gap is formed between the distal end surface of the first protruding portion 31 and the rear surface 62 of the housing 60. The gap has a small value to the extent that the distal end of the first protruding portion 31 can be brought into contact with the rear surface 62 of the housing 60 in a case where a load is applied to the front surface 61 of the housing 60. In a state in which no load is applied to the front surface 61 of the housing 60, the gap may not be present.

A recessed portion may be formed at a position of the rear surface 62 of the housing 60 facing the distal end of the first protruding portion 31, and the first protruding portion 31 may be fitted into the recessed portion in a state in which no load is applied to the front surface 61 of the housing 60. According to this configuration, the first protruding portion 31 and the recessed portion can be used for positioning of the radiation detection panel 10.

In the example shown in FIG. 3, the nine first protruding portions 31 are arranged on the surface 20b in a square lattice pattern in a direction x1, which is one direction of the direction X, and a direction x2, which is one direction of the direction X and is perpendicular to the direction x1. A direction x3 shown in FIG. 3 indicates a direction crossing the direction x1 and the direction x2 at an angle of 45°.

The second protruding portion 32 is a rectangular parallelepiped member extending in the direction X. The length of the second protruding portion 32 in the direction Z is shorter than the length of the first protruding portion 31 in the direction Z by, for example, 2 mm or more so that the arrangement space of the circuit board 40 and the battery 50 can be secured between the second protruding portion 32 and the rear surface 62 of the housing 60.

As shown in FIG. 3, focusing on each of the first protruding portions 31, the second protruding portion 32 is formed so as to connect the first protruding portion 31 of interest to the other first protruding portions 31 adjacent to the first protruding portion 31 in the directions x1, x2, and x3. The state in which the two first protruding portions 31 are connected to each other means that one end of the second protruding portion 32 is in contact with one of the two first protruding portions 31 and the other end of the second protruding portion 32 is in contact with the other one of the two first protruding portions 31.

In this manner, focusing on the three adjacent first protruding portions 31 among the nine first protruding portions 31, the second protruding portion 32 is formed so as to extend along each of three sides of a triangle having the positions of the three first protruding portions 31 as apices, thereby connecting the three first protruding portions 31 to each other.

As shown in FIGS. 2 and 3, the circuit board 40 and the battery 50 are arranged between the second protruding portion 32 and the inner surface of the housing 60 in the space formed between the first protruding portion 31 and the inner surface of the housing 60.

It is desirable to form the first protruding portion 31 and the second protruding portion 32 using a material that can realize weight reduction as well as the load bearing capacity. For example, the first protruding portion 31 and the second protruding portion 32 are formed of a material having a specific gravity of 3.0 or less and a Young's modulus of 1.8 Gpa or more, such as a magnesium alloy, an aluminum alloy, a fiber reinforced resin, a cellulose nanofiber (CNF) reinforced resin, or a resin.

The reinforcing member 30 may be one in which the first protruding portion 31 and the second protruding portion 32 are integrally molded. Alternatively, the reinforcing member 30 may be molded integrally with the support member 20.

In the electronic cassette 1 configured as described above, in a case where a load is applied to the front surface 61 of the housing 60, the distal end surface of the first protruding portion 31 is brought into contact with the inner surface of the rear surface 62 of the housing 60 to receive the load. The load applied to a region of the support member 20 other than the periphery of the first protruding portion 31 is dispersed in the direction X by the second protruding portion 32. Therefore, even in a case where the number of first protruding portions 31 is small, it is possible to obtain the sufficient load bearing capacity.

As described above, according to the electronic cassette 1, the number of first protruding portions 31 can be reduced. For this reason, as shown in FIGS. 2 and 3, it is possible to secure a sufficient space for arranging the circuit board 40 and the battery 50. Therefore, according to the electronic cassette 1, it is possible to improve the load bearing capacity and the space use efficiency.

Figure 4:
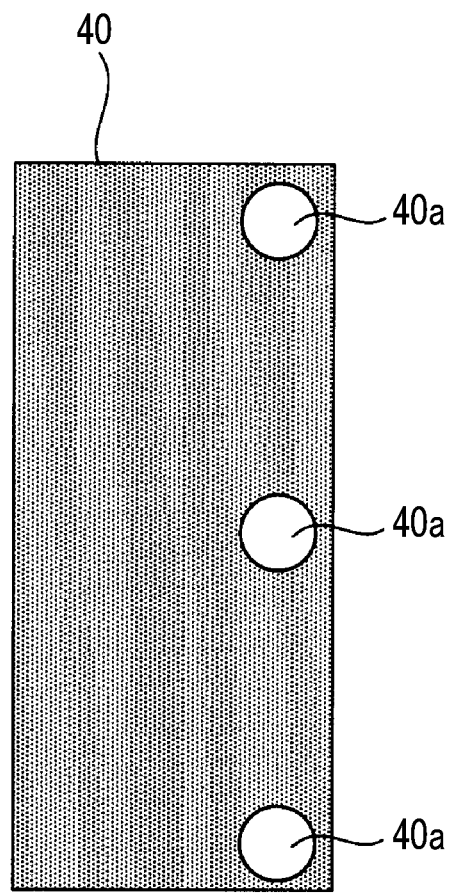
FIG. 4 is a diagram showing a modification example of a circuit board 40 of the electronic cassette 1 shown in FIG. 1.
Figure 5:
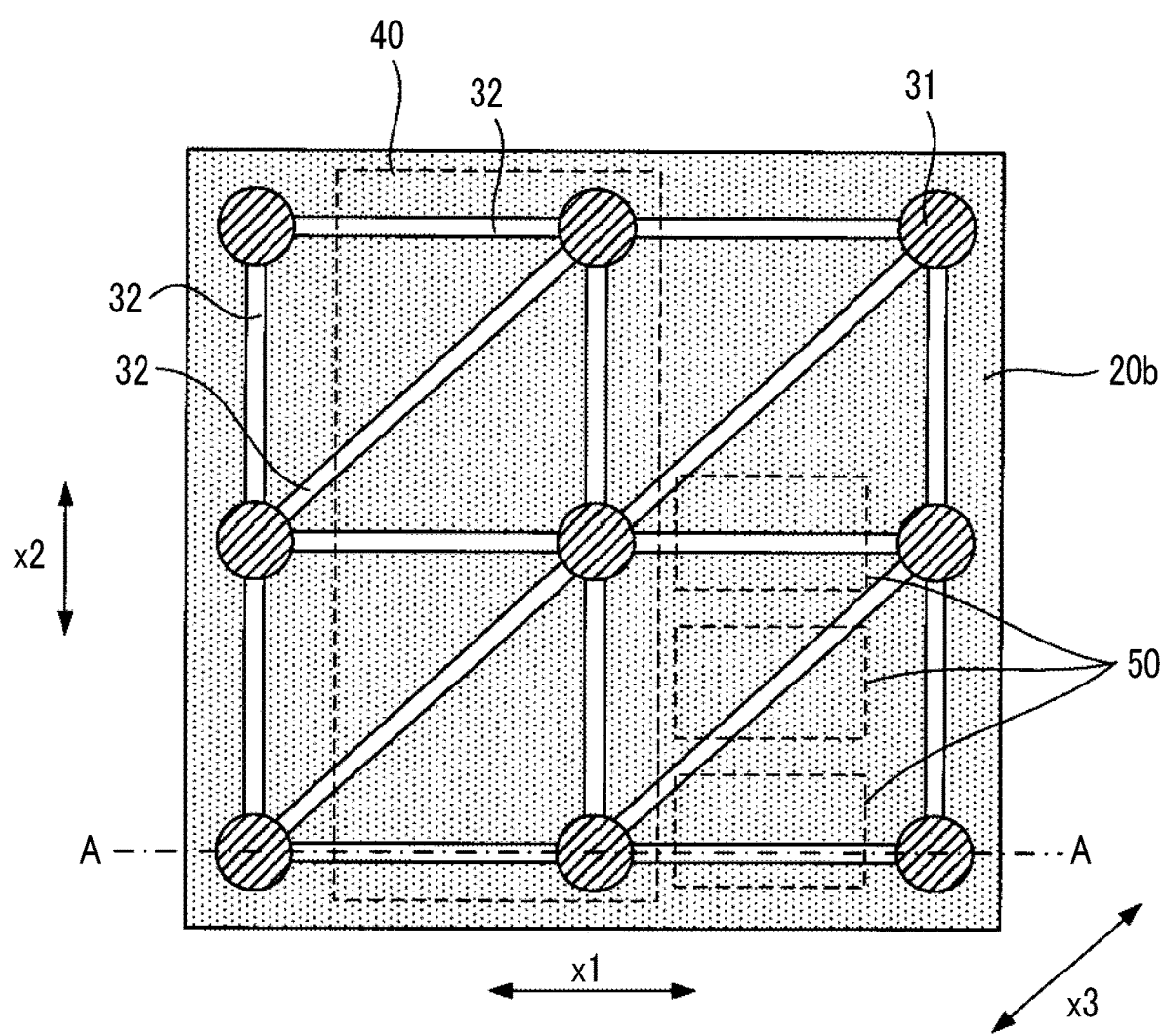
FIG. 5 is a diagram showing an arrangement example of the circuit board 40 shown in FIG. 4.

A through hole 40a through which the first protruding portion 31 can pass can be formed in a surplus region of the circuit board 40 as shown in FIG. 4, and the first protruding portion 31 can pass through the through hole 40a to dispose the circuit board 40 as shown in FIG. 5.

According to this configuration, in a case where the total number of first protruding portions 31 increases or a case where the size of the circuit board 40 is large or in both the cases, the circuit board 40 can be disposed without problems between the support member 20 and the inner surface of the housing 60.

In the electronic cassette 1, as shown in FIG. 3, the number of first protruding portions 31 is nine. However, as long as the number of first protruding portions 31 is three or more, it is possible to form the second protruding portion 32 along the three sides of the triangle described above.

Figure 6:
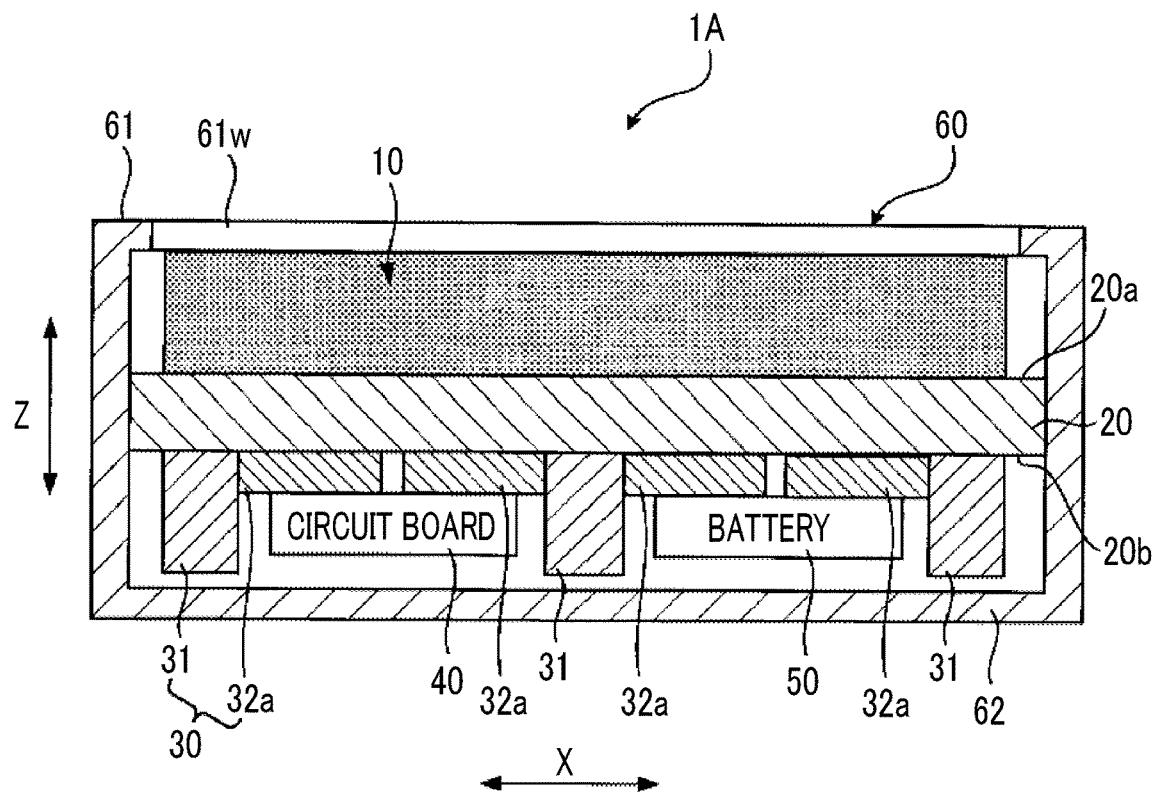
FIG. 6 is a diagram showing a cross section of an electronic cassette 1A that is a first modification example of the electronic cassette 1 shown in FIG. 1, and is a cross-sectional view corresponding to FIG. 2.

FIG. 6 is a diagram showing a cross section of an electronic cassette 1A that is a first modification example of the electronic cassette 1 shown in FIG. 1, and is a cross-sectional view corresponding to FIG. 2.

The electronic cassette 1A has the same configuration as the electronic cassette 1 except that the second protruding portion 32 is changed to a second protruding portion 32a.

The second protruding portion 32a has a configuration in which each second protruding portion 32 shown in FIGS. 2 and 3 is separated into two in the middle. Thus, even in a case where only one end portion of the second protruding portion 32a is in contact with the first protruding portion 31, the same effect as in the electronic cassette 1 can be obtained. In addition, as in the electronic cassette 1, according to the configuration in which both the end portions of the second protruding portion 32 are in contact with the first protruding portion 31, the rigidity of the support member 20 can be further enhanced.

According to the electronic cassette 1A, even in a case where there is a protrusion extending to the upper side in FIG. 6 on the circuit board 40, the circuit board 40 can be stably disposed by making the protrusion pass through a gap between the second protruding portions 32a. In addition, according to this configuration, even in a case where the thickness of the circuit board 40 is large due to a protrusion on the circuit board 40, there is no need to increase the length of the first protruding portion 31 in the direction Z or reduce the length of the second protruding portion 32a in the direction Z. Therefore, it is possible to reduce the thickness of the electronic cassette 1A and to improve the load bearing capacity of the electronic cassette 1A.

Figure 7:
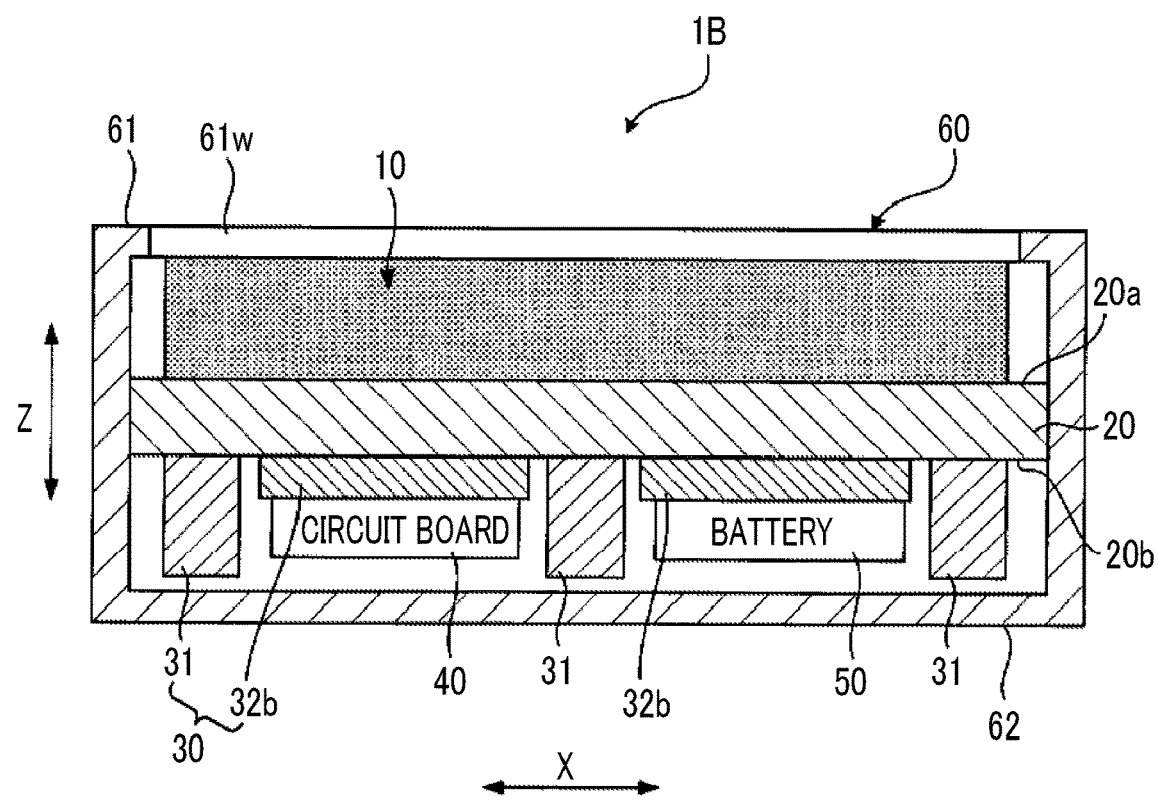
FIG. 7 is a diagram showing a cross section of an electronic cassette 1B that is a second modification example of the electronic cassette 1 shown in FIG. 1, and is a cross-sectional view corresponding to FIG. 2.

FIG. 7 is a diagram showing a cross section of an electronic cassette 1B that is a second modification example of the electronic cassette 1 shown in FIG. 1, and is a cross-sectional view corresponding to FIG. 2.

The electronic cassette 1B has the same configuration as the electronic cassette 1 except that the second protruding portion 32 is changed to a second protruding portion 32b.

The second protruding portion 32b has a configuration in which both end portions of each second protruding portion 32 shown in FIGS. 2 and 3 are not in contact with the first protruding portion 31. Thus, even in a case where both end portions of the second protruding portion 32 are not in contact with the first protruding portion 31, the same effect as in the electronic cassette 1 can be obtained. According to this configuration, since it is possible to reduce the volume of the second protruding portion 32b, it is possible to reduce the weight of the electronic cassette 1B.

Figure 8:
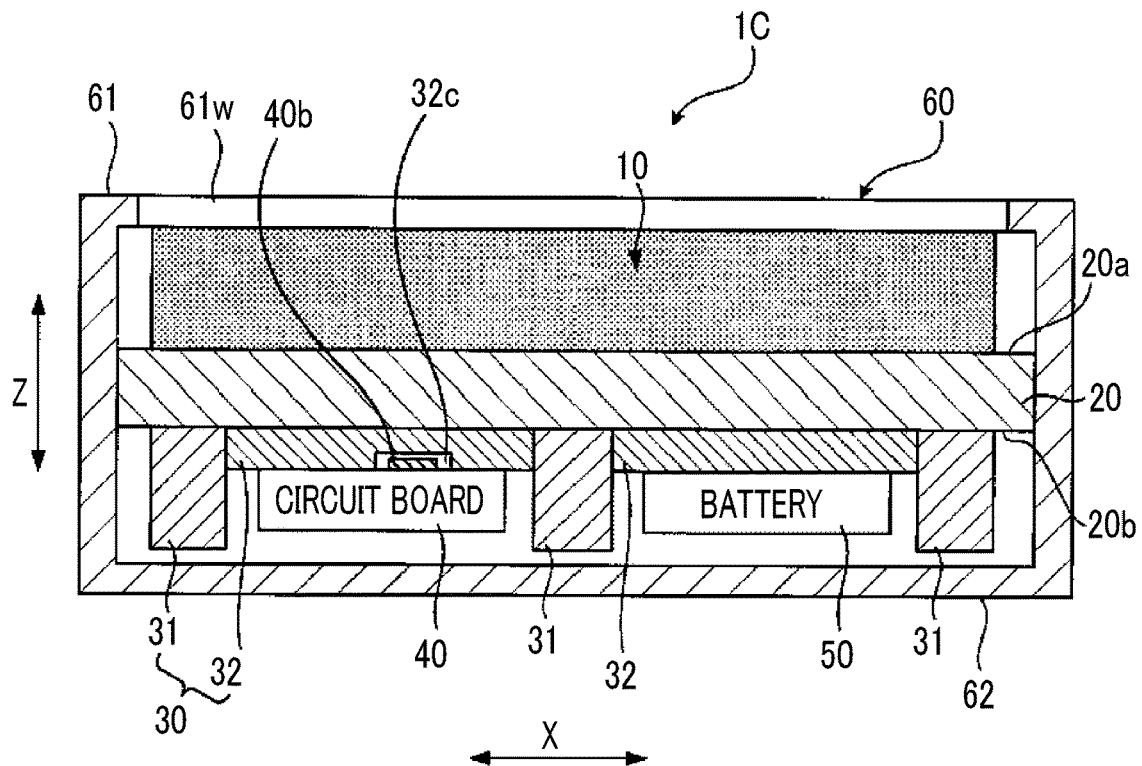
FIG. 8 is a diagram showing a cross section of an electronic cassette 1C that is a third modification example of the electronic cassette 1 shown in FIG. 1, and is a cross-sectional view corresponding to FIG. 2.

FIG. 8 is a diagram showing a cross section of an electronic cassette 1C that is a third modification example of the electronic cassette 1 shown in FIG. 1, and is a cross-sectional view corresponding to FIG. 2.

The electronic cassette 1C has the same configuration as the electronic cassette 1 except that a notched portion 32c is formed in a top portion of the housing 60 on the rear surface 62 side in at least some of the second protruding portions 32 included in the reinforcing member 30.

According to the electronic cassette 1C, even in a case where there is a protrusion 40b extending to the upper side in FIG. 8 on the circuit board 40, the circuit board 40 can be stably disposed by housing the protrusion 40b in the notched portion 32c of the second protruding portion 32 as shown in FIG. 8. In addition, according to this configuration, even in a case where the thickness of the circuit board 40 is large due to a protrusion on the circuit board 40, there is no need to increase the length of the first protruding portion 31 in the direction Z or reduce the length of a second protruding portion 32 in the direction Z. Therefore, it is possible to reduce the thickness of the electronic cassette 1C and to improve the load bearing capacity of the electronic cassette 1C.

Figure 9:
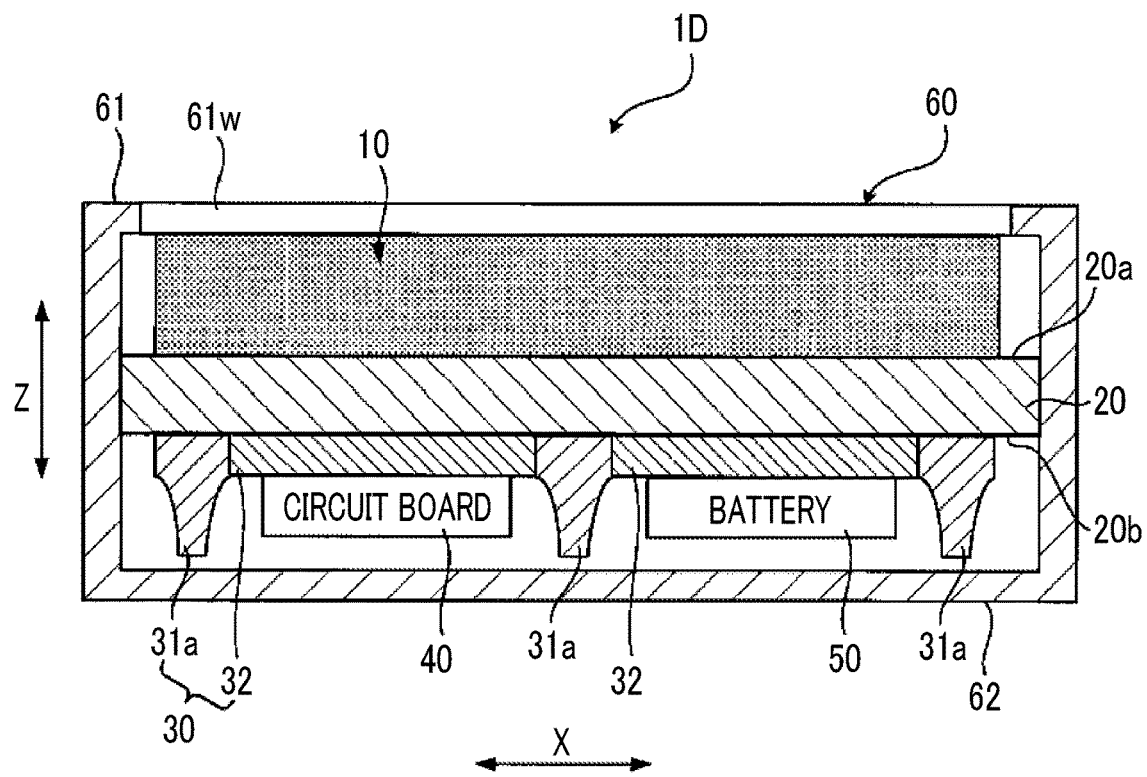
FIG. 9 is a diagram showing a cross section of an electronic cassette 1D that is a fourth modification example of the electronic cassette 1 shown in FIG. 1, and is a cross-sectional view corresponding to FIG. 2.

FIG. 9 is a diagram showing a cross section of an electronic cassette 1D that is a fourth modification example of the electronic cassette 1 shown in FIG. 1, and is a cross-sectional view corresponding to FIG. 2.

The electronic cassette 1D has the same configuration as the electronic cassette 1 except that the first protruding portion 31 is changed to a first protruding portion 31a.

The first protruding portion 31a is formed by changing the shape of the first protruding portion 31. Specifically, the first protruding portion 31a has a tapered shape in which the width of the first protruding portion 31a in the direction X increases from the distal end of the first protruding portion 31a toward the proximal end.

By adopting such a tapered shape, it is possible to further increase the load bearing capacity.

Figure 10:
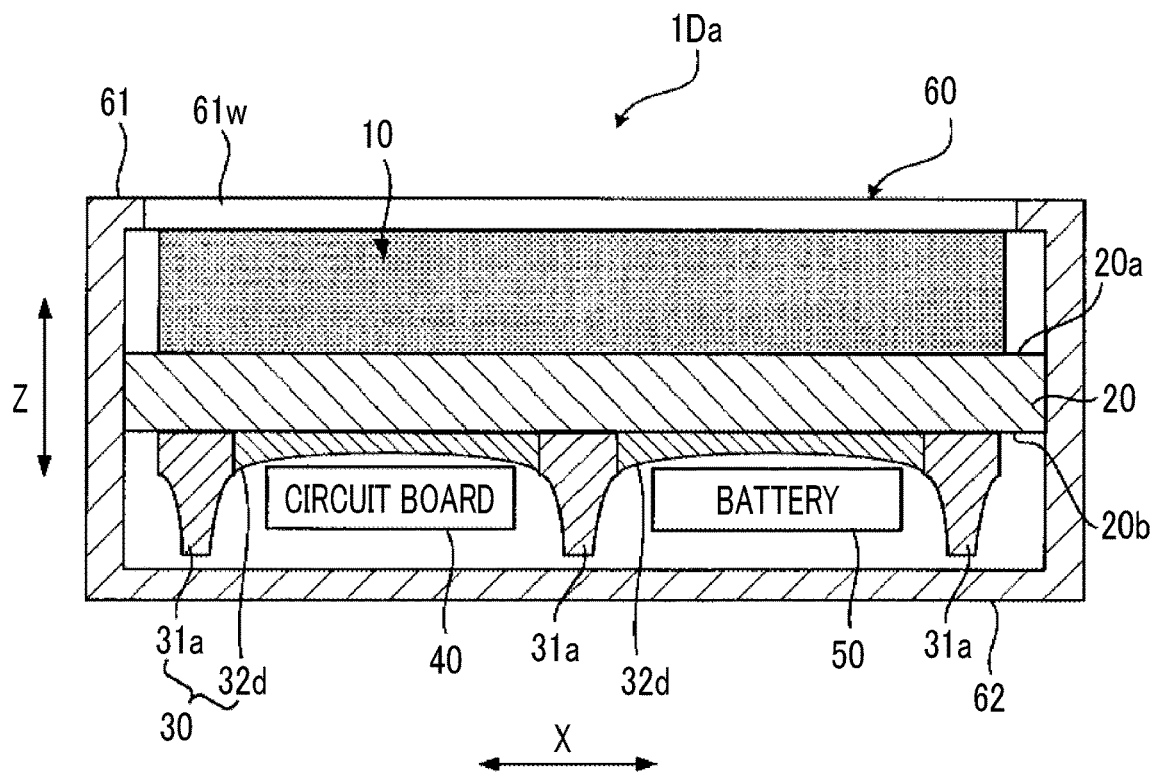
FIG. 10 is a diagram showing a cross section of an electronic cassette 1Da that is a fifth modification example of the electronic cassette 1 shown in FIG. 1, and is a cross-sectional view corresponding to FIG. 2.

FIG. 10 is a diagram showing a cross section of an electronic cassette 1Da that is a fifth modification example of the electronic cassette 1 shown in FIG. 1, and is a cross-sectional view corresponding to FIG. 2.

The electronic cassette 1Da has the same configuration as the electronic cassette 1D except that the second protruding portion 32 is changed to a second protruding portion 32d.

The second protruding portion 32d is different from the second protruding portion 32 in that the distal end portion of the second protruding portion 32d in the direction Z has a recessed shape that is recessed toward the support member 20 side. According to this configuration, since it is possible to reduce the volume of the second protruding portion 32d, it is possible to reduce the weight of the electronic cassette 1Da.

In the electronic cassette 1Da, the first protruding portion 31a can be changed to the first protruding portion 31. Even with this configuration, it is possible to reduce the weight of the electronic cassette 1Da.

The second protruding portion 32a of the electronic cassette 1A shown in FIG. 6 may be made to have a recessed shape that is recessed toward the support member 20 side, or the second protruding portion 32b of the electronic cassette 1B shown in FIG. 7 may be made to have a recessed shape that is recessed toward the support member 20 side.

Figure 11:
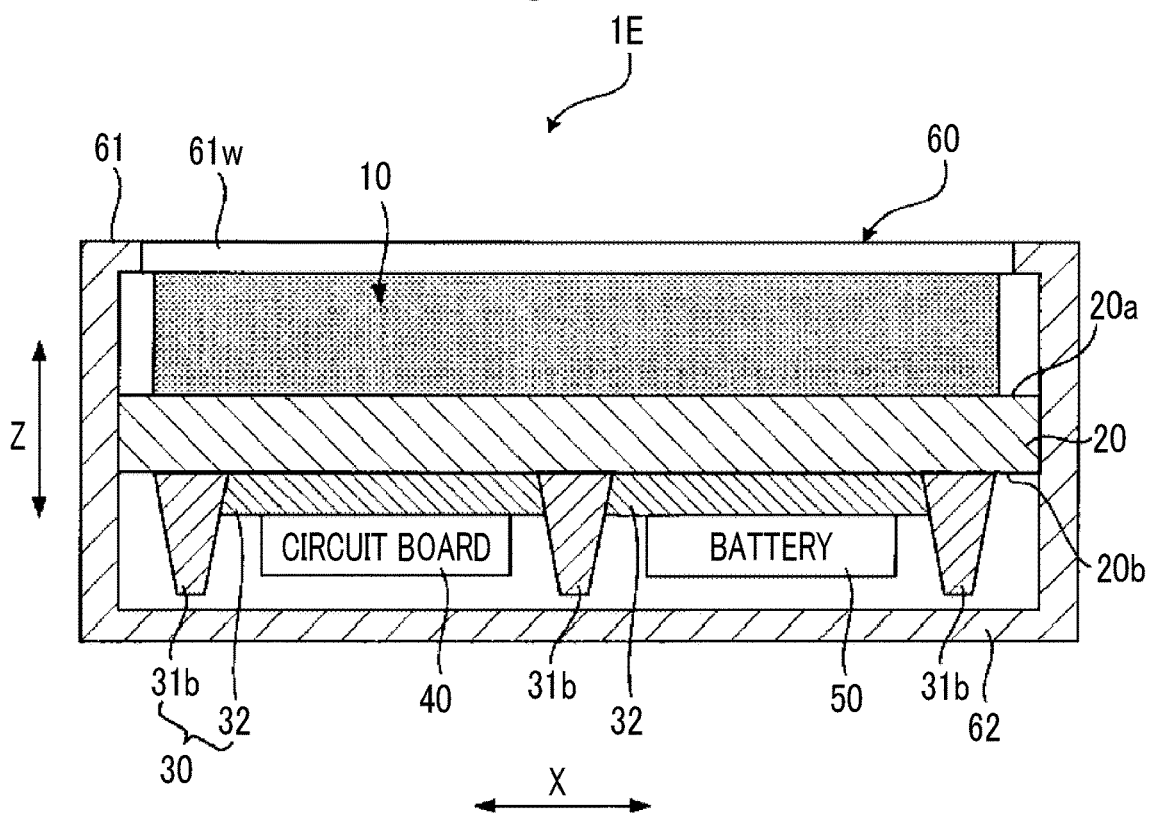
FIG. 11 is a diagram showing a cross section of an electronic cassette 1E that is a sixth modification example of the electronic cassette 1 shown in FIG. 1, and is a cross-sectional view corresponding to FIG. 2.

FIG. 11 is a diagram showing a cross section of an electronic cassette 1E that is a six modification example of the electronic cassette 1 shown in FIG. 1, and is a cross-sectional view corresponding to FIG. 2.

The electronic cassette 1E has the same configuration as the electronic cassette 1 except that the first protruding portion 31 is changed to a first protruding portion 31b.

The first protruding portion 31b is formed by changing the shape of the first protruding portion 31. Specifically, the first protruding portion 31b has a shape in which a top portion of a cone or a pyramid is cut along the direction X, and has a tapered shape in which the width of the first protruding portion 31b in the direction X increases from the distal end of the first protruding portion 31b toward the proximal end similarly to the first protruding portion 31a in FIG. 9.

By adopting such a tapered shape, it is possible to further increase the load bearing capacity.

Figure 12:
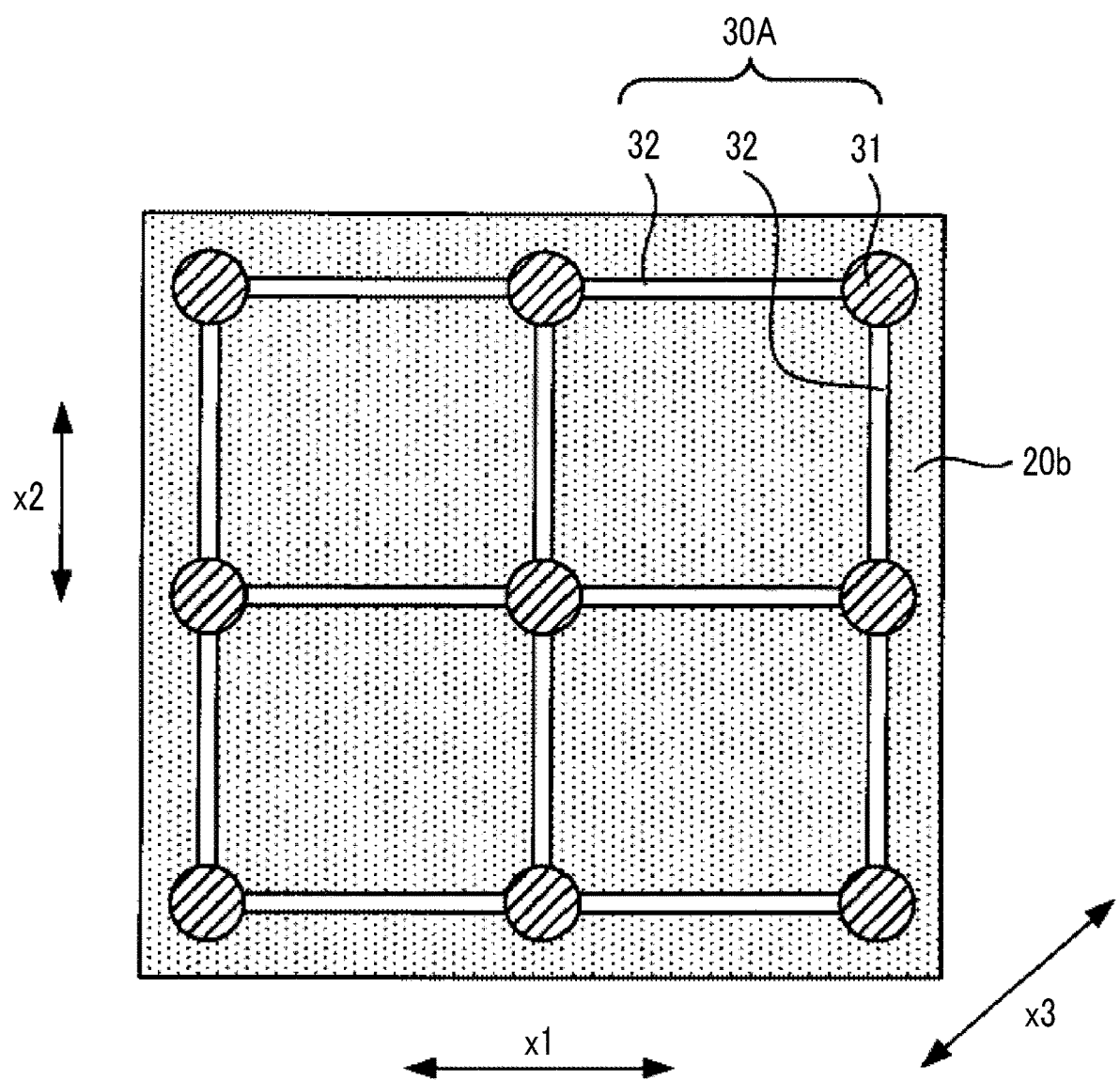
FIG. 12 is a diagram showing a reinforcing member 30A that is a first modification example of the reinforcing member 30 shown in FIG. 3.

FIG. 12 is a diagram showing a reinforcing member 30A that is a first modification example of the reinforcing member 30 shown in FIG. 3.

In the reinforcing member 30A shown in FIG. 12, only the arrangement of the second protruding portion 32 is changed from that in FIG. 3.

Focusing on each of the first protruding portions 31, the second protruding portion 32 of the reinforcing member 30A shown in FIG. 12 is formed so as to connect the first protruding portion 31 of interest to the other first protruding portions 31 adjacent to the first protruding portion 31 in the directions x1 and x2.

That is, focusing on the four adjacent first protruding portions 31 among the nine first protruding portions 31, the second protruding portion 32 of the reinforcing member 30A shown in FIG. 12 is formed so as to extend along each of four sides of a quadrangle having the positions of the four first protruding portions 31 as apices, thereby connecting the four first protruding portions 31 to each other.

Even with such a configuration of the reinforcing member 30A, the support member 20 can be reinforced by the second protruding portion 32. As a result, it is possible to improve the load bearing capacity.

Figure 13:
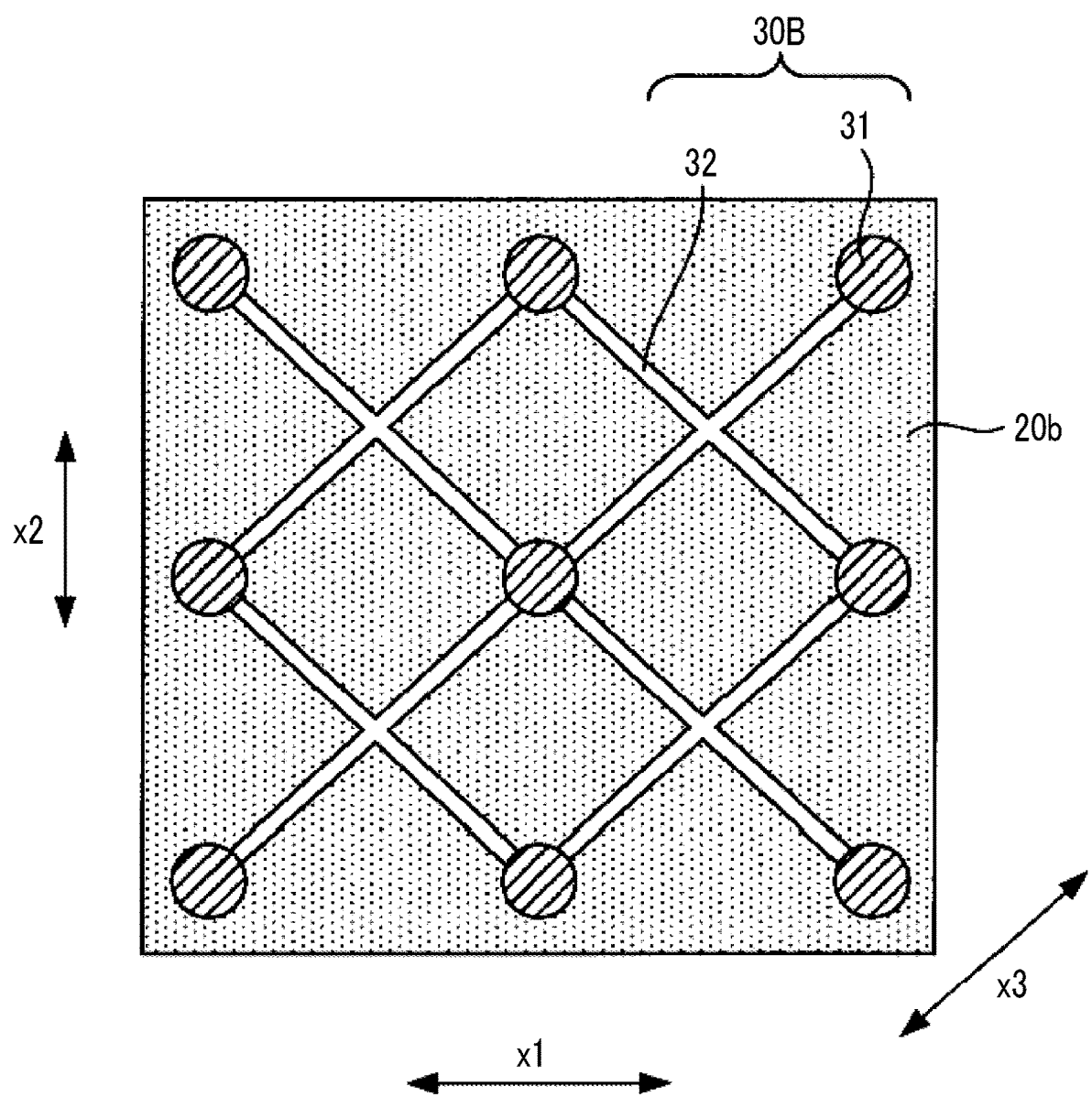
FIG. 13 is a diagram showing a reinforcing member 30B that is a second modification example of the reinforcing member 30 shown in FIG. 3.

FIG. 13 is a diagram showing a reinforcing member 30B that is a second modification example of the reinforcing member 30 shown in FIG. 3.

In the reinforcing member 30B shown in FIG. 13, only the arrangement of the second protruding portion 32 is changed from that in FIG. 3.

Focusing on each of the first protruding portions 31, the second protruding portion 32 of the reinforcing member 30B shown in FIG. 13 is formed so as to connect the first protruding portion 31 of interest to the other first protruding portions 31 adjacent to the first protruding portion 31 in the direction x3 and a direction perpendicular to the direction x3.

That is, focusing on the four adjacent first protruding portions 31 among the nine first protruding portions 31, the second protruding portion 32 of the reinforcing member 30B shown in FIG. 13 is formed so as to extend along each of two diagonal lines of a quadrangle having the positions of the four first protruding portions 31 as apices, thereby connecting the two first protruding portions 31 on each diagonal line to each other.

Even with such a configuration of the reinforcing member 30B, the support member 20 can be reinforced by the second protruding portion 32. As a result, it is possible to improve the load bearing capacity.

In the reinforcing members 30A and 30B shown in FIGS. 12 and 13, in a case where the number of first protruding portions 31 is four or more, it is possible to form the second protruding portion 32 along the four sides or the diagonal lines of the quadrangle described above.

Figure 14:
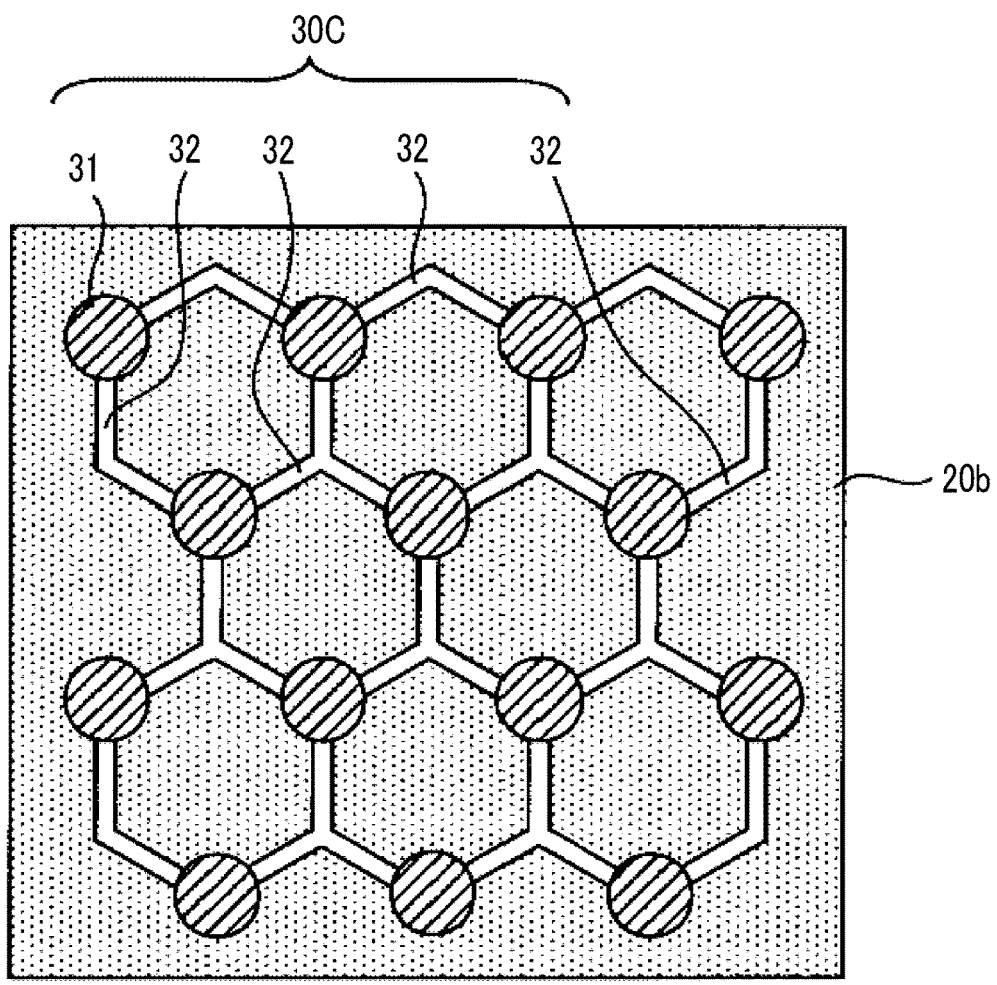
FIG. 14 is a diagram showing a reinforcing member 30C that is a third modification example of the reinforcing member 30 shown in FIG. 3.

FIG. 14 is a diagram showing a reinforcing member 30C that is a third modification example of the reinforcing member 30 shown in FIG. 3.

In the reinforcing member 30C shown in FIG. 14, the number and arrangement of first protruding portions 31 and the arrangement and planar shape of the second protruding portion 32 are changed from those in FIG. 3.

The number of first protruding portions 31 of the reinforcing member 30C shown in FIG. 14 is 14, and the first protruding portions 31 are arranged in a zigzag manner on the surface 20b.

The second protruding portions 32 of the reinforcing member 30C shown in FIG. 14 are arranged such that the V-shaped second protruding portions 32 and the Y-shaped second protruding portions 32 form a honeycomb contour, and the first protruding portion 31 is formed at the intersection position between the second protruding portions 32.

That is, the second protruding portion 32 of the reinforcing member 30C shown in FIG. 14 is formed so as to extend along each side of a hexagon having the positions of the three adjacent first protruding portions 31, among the 14 first protruding portions 31, as apices, thereby connecting the three first protruding portions 31 to each other.

Even with such a configuration of the reinforcing member 30C, the support member 20 can be reinforced by the second protruding portion 32. As a result, it is possible to improve the load bearing capacity.

In the reinforcing member 30C shown in FIG. 14, as long as the number of first protruding portions 31 is three or more, it is possible to form the second protruding portion 32 along each side of the hexagon described above.

Figure 15:
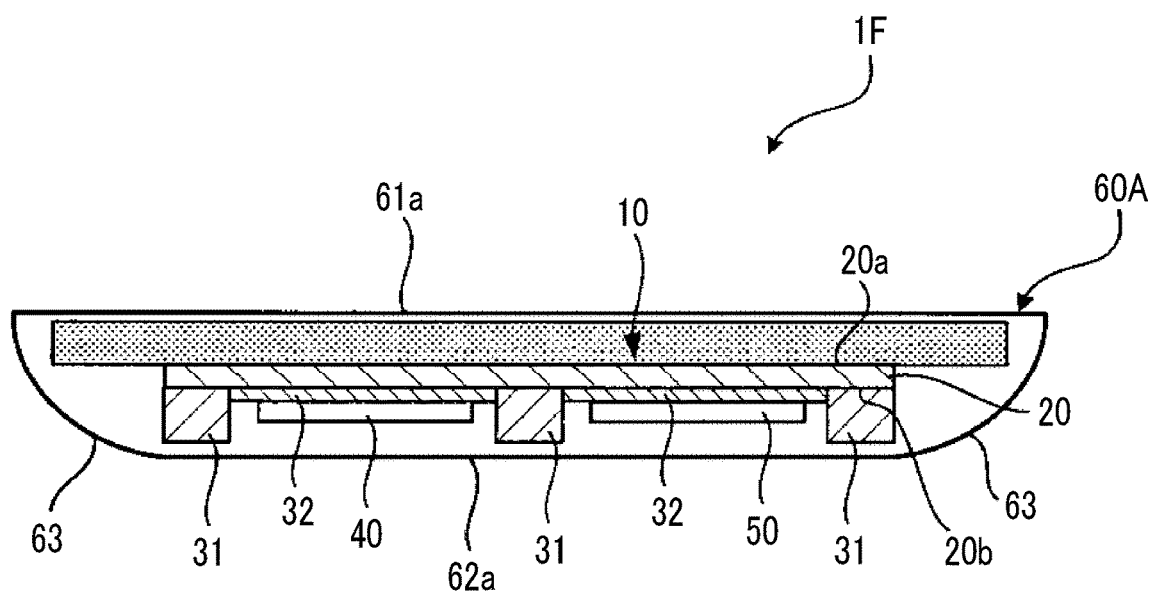
FIG. 15 is a diagram showing the schematic configuration of an electronic cassette 1F that is a seventh modification example of the electronic cassette 1 shown in FIG. 1.
Figure 16:
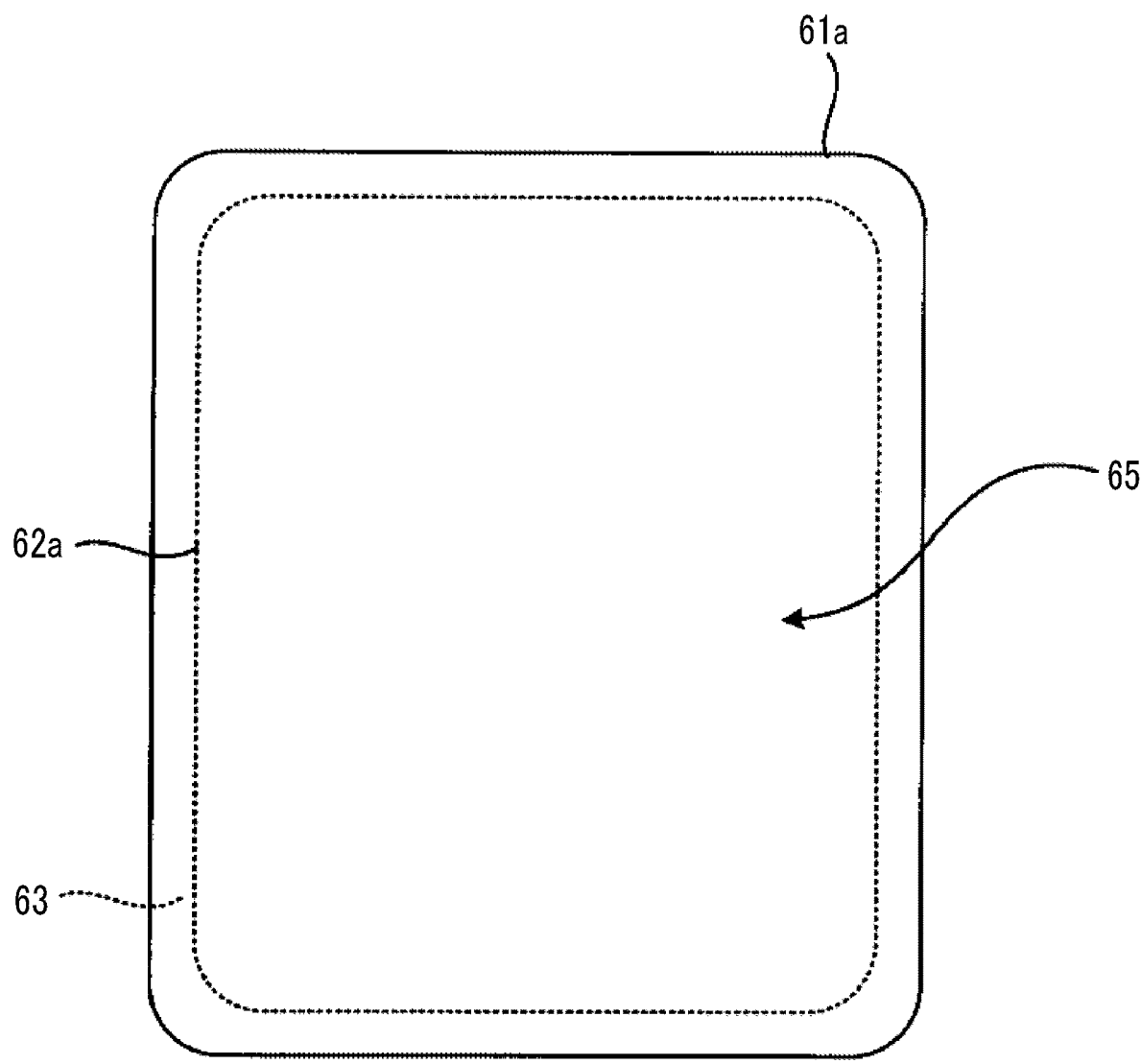
FIG. 16 is a plan view of the electronic cassette 1F shown in FIG. 15 as viewed from the X-ray incidence side.

FIG. 15 is a diagram showing the schematic configuration of an electronic cassette 1F that is a seventh modification example of the electronic cassette 1 shown in FIG. 1. FIG. 16 is a plan view of the electronic cassette 1F shown in FIG. 15 as viewed from the X-ray incidence side.

In the electronic cassette 1F, the housing 60 in the electronic cassette 1 is changed to a housing 60A.

The housing 60A is configured to have, as outer surfaces, a first surface 61a on the X-ray incidence side, a second surface 62a on a side opposite to the first surface 61a, and a curved surface 63 connecting the second surface 62a and the first surface 61a to each other.

As shown in FIG. 16, the second surface 62a is formed on the inner side rather than the first surface 61a as viewed from the direction perpendicular to the first surface 61a.

In the electronic cassette 1F, the reinforcing member 30 configured to include the first protruding portion 31 and the second protruding portion 32 is formed in a range 65 overlapping the second surface 62a in a plan view of FIG. 16. The radiation detection panel 10 is formed outside the range 65, that is, in a portion inside the housing 60A overlapping the curved surface 63 in FIG. 16, but the support member 20 and the reinforcing member 30 are not formed.

In the electronic cassette 1F, in a case where a load is applied to the outside of the range 65, the housing 60A floats up at the placement location along the curved surface 63. That is, almost no load is applied to the space between the curved surface 63 and the first surface 61a. Therefore, by not arranging the reinforcing member 30 in this space, it is possible to reduce the manufacturing cost of the electronic cassette 1F or to reduce the weight.

The modification examples described so far can be appropriately combined and executed. For example, the configuration of the reinforcing member shown in FIGS. 6 to 11 and the configuration of the reinforcing member shown in FIGS. 12 to 14 can be combined. In addition, the configuration shown in FIG. 15 and the configuration shown in FIGS. 6 to 14 can be combined.

In the above description, the radiation detection panel 10 is supported by the support member 20. However, the radiation detection panel 10 may be supported by the housing 60 by being bonded to the front surface 61 of the housing 60 and the transmission plate 61w. In this case, the support member 20 functions as a member that supports the circuit board 40, the battery 50, and the like.

As described above, the following matters are disclosed in this specification.

(1) A radiation detection device comprising: a radiation detection panel; a housing in which the radiation detection panel is housed; a support member that is disposed between a surface of the radiation detection panel on an opposite side to a radiation incidence side and an inner surface of the housing; a plurality of columnar first protruding portions that are formed on a surface of the support member on a side opposite to a surface on the radiation detection panel side; and a second protruding portion that is formed in a region excluding a region, in which the first protruding portions are formed, of the surface of the support member on the opposite side so as to extend along the surface and that has a length in a direction, which is perpendicular to the surface of the support member on the radiation detection panel side, shorter than the first protruding portion.

(2) The radiation detection device described in (1), where the second protruding portion is in contact with the first protruding portion.

(3) The radiation detection device described in (1) or (2), where the second protruding portion connects the two adjacent first protruding portions to each other.

(4) The radiation detection device described in any one of (1) to (3), where three or more first protruding portions are formed, and assuming that n is a natural number of 3 or more, the second protruding portion is formed along each side of a polygon in a case where positions of the n adjacent first protruding portions among the three or more first protruding portions are at least some of apices of the polygon.

(5) The radiation detection device described in (4), where the n is 3, and the polygon is a triangle.

(6) The radiation detection device described in (4), where the n is 3, and the polygon is a hexagon.

(7) The radiation detection device described in any one of (1) to (3), where four or more first protruding portions are formed, and the second protruding portion is formed along a diagonal line of a quadrangle having the four adjacent first protruding portions, among the four or more first protruding portions, as apices.

(8) The radiation detection device described in any one of (1) to (7), where the second protruding portion includes a portion in which a notched portion is formed in a part of a top surface.

(9) The radiation detection device described in any one of (1) to (8), where the first protruding portion has a tapered shape in which a width of the first protruding portion in a direction, which is parallel to the surface of the support member on the radiation detection panel side, increases from a distal end of the first protruding portion toward a proximal end.

(10) The radiation detection device described in any one of (1) to (9), where the second protruding portion has a recessed shape that is recessed toward the support member side.

(11) The radiation detection device described in any one of (1) to (10) that further comprises a circuit board or a power supply unit that is disposed between the inner surface of the housing and the second protruding portion.

(12) The radiation detection device described in any one of (1) to (11), where outer surfaces of the housing has a first surface on the radiation incidence side, a second surface that is a surface on a side opposite to the first surface and that is located on an inner side rather than the first surface as viewed from a direction perpendicular to the first surface, and a curved surface connecting the second surface and the first surface to each other, and the first protruding portion and the second protruding portion are formed in a range overlapping the second surface as viewed from the direction perpendicular to the first surface.

The invention is highly convenient and effective in a case where the invention is applied to an X-ray imaging apparatus and the like.

EXPLANATION OF REFERENCES 1, 1A, 1B, 1C, 1D, 1Da, 1E, 1F: electronic cassette
10: radiation detection panel
11: scintillator
12: light detection substrate
20: support member
20a: support surface
20b: surface
30, 30A, 30B, 30C: reinforcing member
31, 31a, 31b: first protruding portion
32, 32a, 32b, 32d: second protruding portion
32c: notched portion
40: circuit board
40a: through hole
40b: protrusion
50: battery
60, 60A: housing
61w: transmission plate
61: front surface
62: rear surface
61a: first surface
62a: second surface
63: curved surface
65: range

What is claimed is:
1. A radiation detection device comprising:
a radiation detection panel;
a housing in which the radiation detection panel is housed;
a support member that is disposed between a surface of the radiation detection panel on a side opposite to a radiation incidence side and an inner surface of the housing;
a plurality of columnar first protruding portions that are formed on a surface of the support member on an opposite side to a surface of the support member on a side of the radiation detection panel; and
a second protruding portion that is formed at other region of the surface of the support member on the opposite side than regions of the surface of the support member on the opposite side at which the first protruding portions are formed, so as to extend along the surface of the support member on the opposite side and that has a length in a direction, which is perpendicular to the surface of the support member on the side of the radiation detection panel, shorter than the first protruding portions,
wherein three or more of the first protruding portions are provided, and
assuming that n is a natural number of 3 or more, the second protruding portion is formed along each side of a polygon in a case where positions of the n adjacent first protruding portions among the three or more first protruding portions are at least some of apices of the polygon.

2. The radiation detection device according to claim 1, wherein the second protruding portion is in contact with at least one of the first protruding portions.

3. The radiation detection device according to claim 2, wherein the second protruding portion connects the two adjacent first protruding portions to each other.

4. The radiation detection device according to claim 2, wherein the second protruding portion includes a notched portion at a part of a top surface of the second protruding portion.

5. The radiation detection device according to claim 2, wherein at least one of the first protruding portions has a tapered shape in which a width of the first protruding portion in a direction, which is parallel to the surface of the support member on the side of the radiation detection panel, increases from a distal end of the first protruding portion toward a proximal end of the first protruding portion.

6. The radiation detection device according to claim 2, wherein the second protruding portion has a recessed shape that is recessed toward a side of the support member.

7. The radiation detection device according to claim 1, wherein the second protruding portion connects the two adjacent first protruding portions to each other.

8. The radiation detection device according to claim 1, wherein the n is 3, and the polygon is a triangle.

9. The radiation detection device according to claim 1, wherein the n is 3, and the polygon is a hexagon.

10. The radiation detection device according to claim 1, wherein the second protruding portion includes a notched portion at a part of a top surface of the second protruding portion.

11. The radiation detection device according to claim 1, wherein at least one of the first protruding portions has a tapered shape in which a width of the first protruding portion in a direction, which is parallel to the surface of the support member on the side of the radiation detection panel, increases from a distal end of the first protruding portion toward a proximal end of the first protruding portion.

12. The radiation detection device according to claim 1, wherein the second protruding portion has a recessed shape that is recessed toward a side of the support member.

13. The radiation detection device according to claim 1, further comprising:
a circuit board or a power supply unit that is disposed between the inner surface of the housing and the second protruding portion.

14. The radiation detection device according to claim 1, wherein outer surfaces of the housing include a first surface on the radiation incidence side, a second surface that is a surface on a side opposite to the first surface and that is located at an inner side than the first surface as viewed from a direction perpendicular to the first surface, and a curved surface connecting the second surface and the first surface to each other, and
the first protruding portions and the second protruding portion are formed in a range overlapping the second surface as viewed from the direction perpendicular to the first surface.

15. The radiation detection device comprising,
a radiation detection panel;
a housing in which the radiation detection panel is housed;
a support member that is disposed between a surface of the radiation detection panel on a side opposite to a radiation incidence side and an inner surface of the housing;
a plurality of columnar first protruding portions that are formed on a surface of the support member on an opposite side to a surface of the support member on a side of the radiation detection panel; and
a second protruding portion that is formed at other region of the surface of the support member on the opposite side than regions of the surface of the support member on the opposite side at which the first protruding portions are formed, so as to extend along the surface of the support member on the opposite side and that has a length in a direction, which is perpendicular to the surface of the support member on the side of the radiation detection panel, shorter than the first protruding portions,
wherein four or more of the first protruding portions are provided, and
the second protruding portion is formed along a diagonal line of a quadrangle having four adjacent first protruding portions, among the four or more first protruding portions, as apices.

16. The radiation detection device according to claim 15, wherein the second protruding portion is in contact with at least one of the first protruding portions.

* * * * *